(12) United States Patent
Sehgal

(10) Patent No.: US 6,858,011 B2
(45) Date of Patent: Feb. 22, 2005

(54) METHOD AND APPARATUS TO CONTROL MICROBUBBLE DESTRUCTION DURING CONTRAST-ENHANCED ULTRASOUND IMAGING, AND USES THEREFOR

(75) Inventor: Chandra M. Sehgal, Wayne, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 24 days.

(21) Appl. No.: 10/252,642

(22) Filed: Sep. 23, 2002

(65) Prior Publication Data

US 2003/0092991 A1 May 15, 2003

Related U.S. Application Data

(60) Provisional application No. 60/323,927, filed on Sep. 21, 2001.

(51) Int. Cl.$^7$ ................................................ A61B 8/14
(52) U.S. Cl. ...................................................... 600/458
(58) Field of Search .............................. 600/407–471; 424/9.51, 9.52, 9.53; 367/7, 11, 130, 138; 128/916; 73/602–630

(56) References Cited

U.S. PATENT DOCUMENTS 5,944,666 A * 8/1999 Hossack et al. ............. 600/458
6,397,098 B1 * 5/2002 Uber et al. .................. 600/431

OTHER PUBLICATIONS

Arger, P.F., et al, "Evaluation of Change in Blood Flow by Contrast–Enhanced Power Doppler Imaging During Norepinephrine–Induced Renal Vasoconstriction," *Journal of Ultrasound in Medicine* 18:843–851 (1999).

Hedrick, W.R., et al, "Ultrasound Physics and Instrumentation," 3rd Edition, Mosby, Inc. St Louis. (1995).

Kaul, S., "Quantitation of Myocardial Perfusion With Contrast Echocardiography," *American Journal of Cardiac Imaging* 5(3):200–216 (1991).

Porter, T.R, et al, "Transient Myocardial Contrast After Initial Exposure To Diagnostic Ultrasound Pressure With Minute Doses of Intravenously Injected Microbubbles," *Circulation* 92:2391–2395, (1995).

Rovai, D., et al, "Role of Echo–Contrast in Quantitative Analysis" NC Nanda and R. Schlief (eds.), *Kluwer Academic Press*, Dordrecht, Netherlands 341–357 (1993).

Sehgal, C.M., et al, "Mathematical Modeling of the Dilution Curves For Ultrasonographic Contrast Agents," *Journal of Ultrasound In Medicine* 16:471–479 (1997).

Sehgal, C.M. et al, "Sonographic Enhancement of Renal Cortex By Contrast Media," *Journal of Ultrasound in Medicine* 14:741–748 (1995).

Sehgal, C. M., et al, "Comparison of Power Doppler and B–Scan Sonography for Renal Imaging Using a Sonographic Contrast Agent," *Journal of Ultrasound in Medicine* 17:751–756 (1998).

Sehgal, C. M., et al, "Quantitative Vascularity of Breast Masses by Doppler Imaging: Regional Variations and Diagnostic Implications," *Amer. Inst. of Ultrasound in Medicine* 19:427–440 (2000).

(List continued on next page.)

Primary Examiner—Ali Imam
(74) Attorney, Agent, or Firm—Evelyn H. McConathy; Dilworth Paxson LLP

(57) ABSTRACT

Methods and apparatus are provided for controlling fluid flow or perfusion, wherein gas-filled microbubbles are used as ultrasound contrast-enhancing agents, and wherein the method comprises separating the removal of the contrast agent due to flow from the removal of the contrast agent due to bubble destruction for enhanced imaging processes. By varying exposure of the microbubbles to ultrasound, the method and apparatus apply the changes observed in the images to measure flow and vascularity, to improve visualization of blood flow and blood vessels, and to guide delivery of drugs locally to the site of imaging.

29 Claims, 10 Drawing Sheets

OTHER PUBLICATIONS

Wei, K, et al, "Quantitation of Myocardial Blood Flow With Ultrasound–Induced Destruction of Microbubbles Administered as a Constant Venous Infusion," *Circulation* 97:473–483 (1998).

Wei, K., et al, "Quantification of Renal Blood Flow With Contrast–Enhanced Ultrasound," *J. Am. College of Cardiology* 37(4):1135–1140 (2001).

Zierler, K.L., "Theoretical Basis of Indicator–Dilution Methods for Measuring Flow and Volume," *Circulation Research* X:393–407 (1962).

* cited by examiner

METHOD AND APPARATUS TO CONTROL MICROBUBBLE DESTRUCTION DURING CONTRAST-ENHANCED ULTRASOUND IMAGING, AND USES THEREFOR

REFERENCE TO RELATED APPLICATIONS

This application claims priority to U.S. Provisional Applications No. 60/323,927, filed Sep. 21, 2001, the content of which is herein incorporated by reference.

FIELD OF THE INVENTION

The present invention relates to the field of contrast agent-enhanced ultrasound imaging. In particular, the invention relates to controlling the destruction of bubbles by varying exposure to ultrasound and using the changes observed in the images to measure flow and vascularity, improve visualization of blood vessels, and guide delivery of drugs locally to the site of imaging.

BACKGROUND OF THE INVENTION

Tissues and organs of animals and humans develop characteristic vascular architecture to meet specific nutritional and physiologic requirements. Each vascular system comprises networks of large and small blood vessels, wherein each vessel has a different flow rate and function. Under various physiological and pathological conditions, new micro-vessels are formed from existing vasculature. This process of new vessel formation, called angiogenesis, occurs through tightly regulated processes under normal physiological situations.

When these tight controls are breached, uncontrolled angiogenesis ensues. This is often accompanied by the development and progression of a variety of inflammatory, neoplastic, ocular and other diseases. In each situation, however, there is a need to measure blood flow through new and existing blood vessels.

Doppler ultrasound is currently used to measure blood flow through relatively large blood vessels (e.g., >0.2–0.5 mm diameter). However, it is not possible to use Doppler ultrasound to measure the flow through small or newly developed angiogenic vessels. This is, in part, due to the weakness of the signal from the blood moving through such tiny vessels. The use of ultrasound contrast agents could alleviate the signal problem; however, the majority of contrast agents used to enhance ultrasound gray-scale (GS) and Doppler (D) images consist of microbubbles. When these agents are injected, the ultrasound images are enhanced over time, but their use to date for measuring the flow in small vessels has been very limited because the microbubbles are unstable at ambient pressure, causing the bubbles to collapse.

Many studies have demonstrated the use of ultrasound contrast agents (UCA) to enhance images and to determine tissue vascularity, perfusion and blood flow. The image-enhancement versus time plots (often referred to as dilution curves, or video-density-time-curves, or time-intensity (TI) plots) follow a skewed bell-shaped curve with characteristics similar to those observed for indicator dilution curves. However, it has been observed that the microbubbles that produce enhancement are destroyed by the pulses of ultrasound used for constructing images (Porter et al., *Circulation* 92:2391–2395 (1995)).

Gas filled microbubbles that are used in contrast-enhanced imaging are hemodynamically inert and have a rheology similar to that of red blood cells. They are also small and uniform in size, making them less prone to axial streaming or geometric exclusion than has been reported with the use of larger radiolabeled microspheres. Furthermore, their size permits the microbubbles to remain entirely intravascular. Repeated measurements are possible because the microbubbles are rapidly cleared from circulation following administration, but image enhancement is short-lived.

To overcome this problem, techniques related to intermittent imaging have been proposed in which the scanner is turned on/off at a predetermined interval or with EKG gating (Porter et al., 1995). However, while that approach prolongs the time of enhancement, it does not provide quantitative measurements of blood flow or of any other related parameters.

A method based on replenishment of bubbles in scan plane was proposed by Wei and coworkers (Wei et al., *Circulation* 97:473–83 (1998); Wei et al., *J. Am. College of Cardiology* 37(4):1135–1140 (2001)). The method is conducted by infusing contrast agent and measuring the replenishment of bubbles as a function of scan interval. The flow velocity and flow rates are derived from the measurement of initial increase in the rate-of-replenishment and the leveling of video intensity value.

Nevertheless, the method of Wei et al. has several limitations. It only works when long infusions of contrast agent are made, and over this entire duration, a steady state of contrast must be achieved. The interval between images acquired is usually large, and can be as high as 30 seconds. During this interval, there is considerable motion, making it difficult to keep the plane fixed during data acquisition. Moreover, the method also requires image matching for background subtraction, which in view of the motion can be cumbersome and difficult to implement. Furthermore, the method fails to take into consideration the attenuation effect of the overlying tissue, or the bubble destruction during the transit of ultrasound through the scan plane.

In the early stages of ultrasound contrast development, methods similar to those used in tracer techniques were proposed, using ultrasound contrast agents to measure blood flow and perfusion (Rovai et al., 1993, In *Role of Echo-Contrast in Quantitative Analysis*, (Nanda & Schlief, eds), Kluwer Academic Press, Dordrecht, Netherlands, pp. 341–357; Kaul, *Am. J. Cardiac Imaging* 5(3):200–216 (1991); Sehgal et al., *J. Ultrasound Med.* 16:471–479 (1997); Sehgal et al., *J. Ultrasound Med.* 14:741–748 (1995); Sehgal et al., *J. Ultrasound Med.*, 17:751–756 (1998); Arger et al., *J. Ultrasound Med.*, 18:843–851 (1999)). These methods are based on measuring the area under the video-intensity-time curves and the mean transit time following bolus injection of contrast agent.

The problem, however, with the conventional method of image enhancement is that the amount of contrast agent entering an organ not only leaves with the outflow of blood, but it is also removed from circulation due to the destruction of microbubbles. This unique behavior of the ultrasound contrast agent decreases the time taken by the contrast agent to transit or clear through the organ. It also significantly reduces the area under the dilution (time-intensity) curve. Because the blood flow perfusion and the extent of vascularity are related to these measurements, the underestimation of area under the curve and the time of transit lead to erroneous measurements. Therefore, a direct measurement of flow (or any other related parameter) cannot be made from the video-intensity curves unless the effect of bubble destruction is taken into consideration. However, until the present invention, the separation of the two effects, (i.e., (1) removal of the contrast-agent due to flow, versus (2) its removal due to bubble destruction) had not yet been achieved. Thus, there had remained a need for a means and apparatus that would separate the two effects, while at the same time preserving the near real-time capabilities.

SUMMARY

The invention comprises a quantitative method and apparatus for controlling fluid flow, comprising using ultrasound contrast agents for enhanced imaging processes, including gray-scale imaging, harmonic imaging, power Doppler imaging, and the like. The selected contrast-enhancing agent uses gas-filled microbubbles as a tracer to assess blood flow or perfusion. Preferably, the method further comprises separating the effect of removal of the contrast-enhancing agent due to flow, from the effect of its removal due to bubble destruction. It is an object of the invention, therefore, to vary the destruction of the microbubbles by the ultrasound pulses in a controlled fashion to enable physiological measurements of vascularity and blood flow.

Preferred method and apparatus embodiments of the invention permit the exposure of the contrast-enhancing agent to the ultrasound pulses to be varied in a systematic and controlled fashion to obtain multiple dilution curves. Each curve corresponds to a different exposure level, permitting change(s) between or among the resulting curves to be seen and recorded. Yet, all of this is achieved using a single injection of contrast agent. Thus, it is a further object of the invention to detect the change(s) in the dilution curves produced by controlling the time of exposure of the microbubbles in the contrast-enhancing agent to the ultrasound.

It is further provided that the method and apparatus of the invention are used to enhance the visualization of the flow within the blood vessels of organs in a patient.

Also provided is a device to control fluid flow using at least one ultrasound contrast enhancing agent, wherein the device comprises: means for providing controlled flow of the agent in a fluid; means for injecting at least one contrast agent into the fluid flow; an ultrasound scanner, gated at different frame rates to provide images at regular intervals at varying frame rates; and means to compute the image brightness and changes therein during transit of the at least one contrast agent.

In addition, a device is provided to control fluid flow, wherein the device comprises: computer-readable signal bearing medium; means in the medium for computing the image brightness as a function of time; means in the medium for algorithmically separating the effect of the removal of the contrast agent due to flow from the removal of the contrast agent due to bubble destruction. Thus, it is an object of the invention to further provide a device having a means in the medium for automatically computing the blood flow in tissues by varying the exposure of ultrasound contrast enhancing agent to image pulses.

Further provided is a controlled imaging system, wherein the destruction of the microbubbles in the contrast enhancing agent is controlled. By this method, for example, increased destruction of the microbubbles by ultrasound in the initial flow of the agent into the circulation (bloom effect) permits an overview of the area of interest, followed by slowing of the flow to reduce the rate of microbubble destruction to permit a detail view of the vasculature within the area of interest. Alternatively, provided is an image guided drug delivery system, wherein the controlled destruction of the contrast enhancing agent permits controlled drug delivery in terms of time and location of delivery in a patient, when the microbubbles are charged with the drug to be delivered before administration to the patient.

Additional objects, advantages and novel features of the invention will be set forth in part in the description, examples and figures which follow, all of which are intended to be for illustrative purposes only, and not intended in any way to limit the invention, and in part will become apparent to those skilled in the art on examination of the following, or may be learned by practice of the invention.

BRIEF DESCRIPTION OF THE FIGURES

The foregoing summary, as well as the following detailed description of the invention, will be better understood when read in conjunction with the appended figures. For the purpose of illustrating the invention, there are shown in the figures, certain embodiment(s) which are presently preferred. It should be understood, however, that the invention is not limited to the precise arrangements and instrumentalities shown.

FIG. 7A shows mouse tumor before contrast injection. The second and third rows (FIGS. 7B–7G) represent images acquired during the first and second cycle changes in the frame rates. Panels in the first (FIGS. 7B and 7E), second (FIGS. 7A, 7C and 7F), and third (FIGS. 7D and 7G) columns represent image acquisitions at 0.5, 2 and 4 frames per second, respectively.

DESCRIPTION OF PREFERRED EMBODIMENTS OF THE INVENTION

Figure 1:
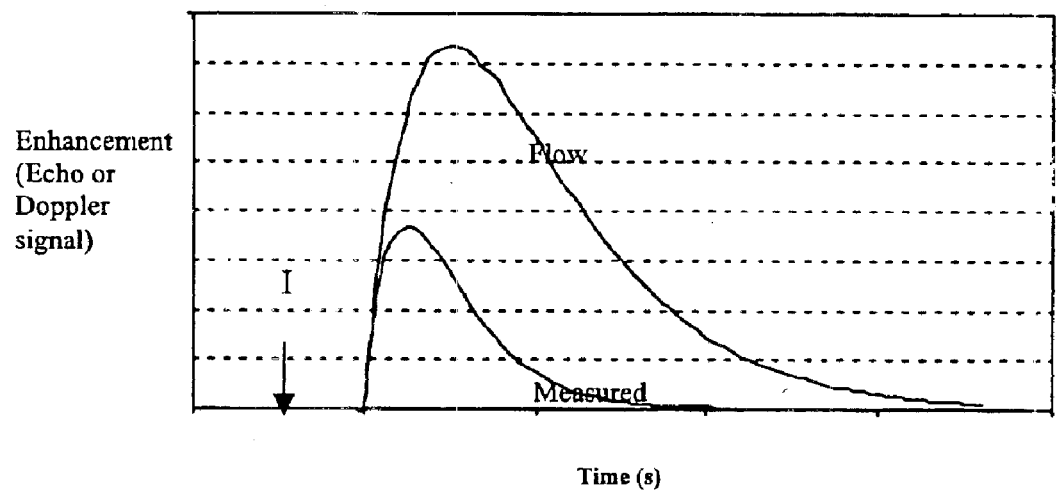
FIG. 1 graphically depicts a conceptual diagram of time-intensity enhancement of ultrasound images. The top curve shows true enhancement and reflects only flow-related changes. The bottom curve shows the measured enhancement curve and reflects changes due to both flow and bubble destruction. I represents the time at which the contrast agent is injected. As the contrast agent arrives in the image plane, the signal (backscatter or Doppler amplitude) increases rapidly. After reaching a peak, the signal decreases due to out flow and bubble destruction.

The invention provides an algorithm, method and apparatus for quantitatively controlling fluid flow, comprising using ultrasound contrast agents comprising gas-filled microbubbles for enhanced imaging processes, including gray-scale imaging, harmonic imaging, power Doppler imaging, and the like. Preferably, the method further comprises separating the effect of removal of the contrast-enhancing agent due to flow, from the effect of its removal due to bubble destruction. The present invention permits separation of the two factors, while preserving near real-time imaging capabilities. Using the preferred method and apparatus, the exposure of contrast agent is varied in a systematic and controlled manner to obtain a plurality of dilution curves (each curve corresponding to a different exposure level), and to observe and record the change(s) between or among the resulting curves. Yet, all of this is achieved using a single injection of contrast agent.

By finding the rate of change in the properties of the dilution curves (e.g., area under the curve, or the change in intensity) with exposure level, true flow is derived. The basis for the method is based on controlled bubble destruction, and identifying the changes resulting from the systematic, controlled variations in the flow. The longer the microbubbles stay in the field of view of the imaging system (that is, the slower the flow), the more they are destroyed. Typical normal ultrasound video is recorded at a rate of 30 frames per second, but the method and apparatus of the present invention permit the measurement of the flow to be reduced in a controlled manner to less than 20 frames per second, or to less than 10 frames per second, or to less than 5 frames per second, and even to less than 1 frame per second. Thus, the present invention works best to measure slow flow, a condition difficult to evaluate with other methods in the prior art. Slow flow through small blood vessels also represents a condition with high clinical and physiological significance often necessary for measuring tissue perfusion.

As described in greater detail in the examples that follow, the preferred embodiments of the present invention have many potential applications in cardiovascular, renal and cancer imaging. The proposed method is applicable to both large and small blood vessels. However, a major impact of this technology is likely to be in measuring blood flow and perfusion through small blood vessels, especially in blood vessels that are difficult to visualize by conventional imaging. Thus, the invention is useful, for example, for measuring renal blood flow changes accompanying diabetes, and organ transplants. It could be used to measure angiogenic and anti-angiogenic activities associated with many cardiovascular diseases, growth of cancer, and wound healing. In addition, it is of value in many treatments involving pharmaceuticals that require a monitoring of changes in blood flow because the present method could be used to evaluate the changes. Of course, the preceding proposed application for the method and apparatus of the present invention are intended merely to be suggestive, but are in no way limiting or comprehensive.

A particular advantage of the present invention is that the method relies upon controlled use of ultrasound imaging, which is noninvasive. It can be used repeatedly on a patient, or in a specific area or tissue, with no known side effects. Yet, unlike other conventional methods used commonly to measure superficial blood flow, ultrasound can be used to visualize blood vessels in organs seated deep inside the body. The dosage of the contrast-enhancing agent need not be changed from that which is routinely used for ultrasound imaging, and any known agent may be used that comprises gas-filled microbubbles. The importance of the invention lies not in the contrast enhancing agent selected, so long as it provides microbubbles as a tracer, it is based upon the systematic and controlled exposure of the microbubbles to the ultrasound waves.

Quantitative Framework for Discounting Bubble Decay and Controlling Fluid Flow

FIG. 1 shows the enhancement of ultrasound and Doppler images with time. Two cases are represented in the figure. The top curve shows a true or idealized enhancement of the images, wherein no bubbles are destroyed. The lower curve shows the measured or observed enhancement. As shown, the measured curve is significantly diminished in amplitude (compared to the idealized curve) due to bubble destruction by the ultrasound pulses.

In both cases, after the contrast agent is injected, there is an increase in image brightness (or color level in Doppler images) due to the inflow of microbubble-scatterers to the imaged organ. This change is rapid and during this interval, the effects of microbubble decay are minimal.

Inflow of the contrast agent is followed by clearance (outflow) of the agent from the organ. Clearance of the contrast agent from the organ occurs over a relatively longer time and follows an inverse exponential function. During this period the microbubbles also collapse and diminish the image enhancement as compared with what would have occurred from outflow of the contrast agent alone. Thus, the observed image enhancement is reduced, as illustrated by the lower curve of FIG. 1.

A mathematical model has been developed by the inventor, describing image brightness ($\Delta B$) as a function of time, t(Sehgal et al., *J. Ultrasound Med.* 16:471–479 (1997)). Although previously derived for gray-scale imaging, the model can also be used to describe the change in the strength of Doppler signal with time during the transit of a contrast agent. According to this model, the change in brightness ($\Delta B$) with time for a log compressed image is represented by Equation 1.

$$\Delta B(t) = 10\left[\log\left(1 + \frac{\sigma_{CM} C(t)}{\sigma_{Tissue}}\right) - 4(\log e)\Delta\alpha(t)L\right] dB, \quad (1)$$

wherein, $\sigma_{Tissue}$=backscatter coefficient from tissues, $\sigma_{CM}$=backscatter coefficient of microbubbles of the contrast medium, $C(t)$=concentration of the contrast media at time t, $\Delta\alpha(t)$ = attenuation due to contrast media, and L = the distance traveled by ultrasound pulses through contrast medium above the region of interest.

Equation 1 can also be used for evaluating Doppler signal, wherein $\Delta B$ represents the signal from those microbubbles that are moving with the blood, rather than all the microbubbles. It is important to note that in the above method the measured brightness change is independent of the overlying tissue, and only depends on the attenuation due to contrast agent that is present in the overlying tissue. The role of this attenuation due to contrast agent is discussed later. For simplicity, when L is small, the second term in the equation can be dropped. This condition of small L generally applies when one is dealing with tumor vasculature, or when the region of enhancement is small. The concentration C(t) of contrast media follows a γ-variate function, as follows:

$$C(t) = C_0 k_F t e^{-(k_P + k_F)} \qquad (2)$$

wherein, $C_0$ = concentration of contrast agent after in the blood pool, $k_F$ = rate constant for flow, and $k_P$ = rate constant for bubble destruction.

Substituting Equation 2 into Equation 1, and simplifying under the condition that the concentration of contrast agent used is small, results in the following equation:

$$\Delta B(t) \approx 10 \left[ \log\left(\frac{\sigma_{CM}}{\sigma_{Tissue}} C_0 k_F t e^{-k_F t}\right) \right] - 10(\log e) k_P t. \qquad (3)$$

Bubble destruction or removal occurs by multiple mechanisms. The bubbles are destroyed by the ambient or vascular pressure; they are removed by lungs and sequestered by phagocytes; and they are destroyed by the transient pressure imposed by acoustic pulses used for imaging. Expressing $k_P = k_{VP} + k_{US}$, in Equation 3, wherein $k_{US}$ and $k_{VP}$ are the rate constants of bubble destruction due to ultrasound pressure and all other mechanisms combined, respectively yield the following:

$$\Delta B(t) = 10\left[\log\left(\frac{\sigma_{CM}}{\sigma_{Tissue}} C_0 k_F t e^{-k_F t}\right)\right] - \qquad (4)$$
$$10(\log e) k_{VP} t - 10(\log e) k_{US} D t,$$

$$= \Delta B_{Flow}(t) - \Delta B_{VP}(t) - 10(\log e) k_{US} D t \qquad (5)$$

wherein, $\Delta B(t)$ and $\Delta B_{Flow}(t)$ are the changes in brightness due to flow and vascular pressure and D is the duty cycle, i.e., the fraction of time that the ultrasound is on. For continuous imaging (i.e., when the ultrasound is on all of the time), D=1, and the time that the ultrasound contrast media is exposed to the ultrasound pulses is equal to the imaging or scanning time.

On the other hand, if the ultrasound images are acquired at a video rate of m frames per second, and the time to acquire each frame is τ, then the contrast agent will be exposed to the ultrasound pulses for mτ seconds for each second of imaging. In other words, D equals mτ. Unfortunately, during the duration τ, the microbubbles are not stationary, rather they are moving due to the blood flow.

If the microbubbles were stationary, they would be exposed to the ultrasound for time τ. However, due to the blood flow, the bubbles of the contrast agent are exposed to the ultrasound pulses for only a short time, i.e., equal to the transit time through the region of interest (ROI) in the image. Thus, the greater the rate of flow, then the shorter the transit time, and the fewer the number of bubbles exposed to the ultrasound. If $MTT_{ROI}$ is the mean time of transit through the ultrasound beam, the effective duty cycle for exposure is calculated as follows:

$$D = m * MTT_{ROI} \qquad (6)$$

Since, the mean time of transit through the ultrasound beam is the ratio of the volume of the blood or blood vessels in the beam ($V_{ROI}$) to the mean flow (F), as follows:

$$D = m \frac{V_{ROI}}{F} \qquad (7)$$

Substituting Equation 7 into Equation 5 equals, $$\Delta B(t) = \Delta B_{Flow}(t) - \Delta B_{VP}(t) - 10(\log e)\frac{k_{US} V_{ROI} t}{F} m. \qquad (8)$$

The area under the dilution curve is equal to the integral of the dilution curve over time. Integrating Equation 8 from times 0 to T yields:

$$\int_0^T \Delta B(t) = \int_0^T \Delta B_{Flow}(t) dt - \int_0^T \Delta B_{VP}(t) dt - 10(\log e)\frac{k_{US} V_{ROI} T^2}{F} m \qquad (9)$$

Equations 8 and 9 are both equivalent and form the basis of the measurements of the preferred embodiment of the present invention. The term on the left side of Equation 9 represents integrated change in brightness (or color level for power Doppler) measured during contrast injection. The terms on the right side of the equation represent the components that contribute to the change. The first term represents change in signal due to inflow and outflow of the contrast agent. The second term represents loss of signal due to vascular pressure or removal of contrast agent by the lungs and reticuloendothelial system. The last term represents loss in signal due to bubble destruction by the ultrasound pulses. If frame rate m is varied, and for each m the area under the curve $$\int_0^T \Delta B(t) dt$$

is measured, then the slope S of $$\int_0^T \Delta B(t) dt$$

versus m is:

$$S = \frac{k_{US} V_{ROI} T^2}{2F} \qquad (10)$$

The intercept, I, of $$\int_0^T \Delta B(t) dt$$

versus m represents the limiting condition, wherein no microbubbles were destroyed by the ultrasound pulses. This value represents the volume of the contrast agent passing through the field of view. Therefore, the ratio S/I represents change in slope per unit concentration of contrast agent. As a result, for the normalized slope, $\overline{S}$, Equation 10 can be recast in the form, $$F = \left(\frac{k_{US}T^2 V_{ROI}}{2}\right)\overline{S} \quad (11)$$

All of the terms on the left side of Equation 11 are known. The parameter $V_{ROI}$ is determined by counting the number of image pixels that have undergone enhancement, T is the time over which integration is performed, and $\overline{S}$ is measured for the time-intensity curve. If the decay constant is not known, Equation 11 can be used to yield the relative flow.

To obtain absolute flow, the images must be calibrated either by using images of other organs with known flow or by using images of flow-phantoms constructed under identical conditions of insonification. For the latter case, the experiment is repeated by measuring flow in a phantom by injecting contrast agent. All of the experimental settings on the measurement instrument are kept fixed, and flow measurements are made by superimposing the same region of interest used for measuring flow through the tissue. Normalizing the tissue flow data with phantom data yields:

$$\frac{F_{Tissue}}{F_{phantom}} = \frac{(\overline{S})_{phantom} V_{Tissue}}{(\overline{S})_{tissue} V_{phantom}} \text{ or } \quad (12)$$

$$F_{Tissue} = \frac{(\overline{S})_{phantom} V_{tissue}}{(\overline{S})_{tissue} V_{phantom}} F_{phantom}. \quad (13)$$

Because all of the terms on the right side of the equation are known, the flow can be directly measured. This approach is novel and advantageous because so long as multiple dilution curves can be obtained with a single injection of contrast agent, one can estimate true flow without the explicit knowledge of the contrast agent decay.

It is important to note that in this disclosure, the area under the curve was used for analysis. An identical analysis can be conducted by observing the change in intensity of the dilution curve with m, starting with Equation 8. If s and i represent slope and intercepts of intensity versus m data, respectively, then:

$$F_{Tissue} = \frac{(s)_{phantom} V_{tissue}}{(s)_{tissue} V_{phantom}} F_{phantom} \quad (14)$$

Both Equations 13 and 14 will yield comparable results, because they use different characteristics of the same dilution curve. In the example discussed above, the exposure of the contrast agent to the ultrasound was varied by changing the frame-rate. It is also important to understand that by using the above-disclosed approach, alternate strategies and equations can be formulated by one of ordinary skill in the art for other parameters that alter the ultrasound exposure, for example the intensity of the pulse, the duty cycle or the pulse sequence. In fact, in situations in which high frame rate is desired, it might be preferable to change one of the above parameters in a controlled fashion, rather than change the frame rate.

Effect of Attenuation of Ultrasound from the Tissues Overlying the Region of Interest If the tissue layer above the region of interest is also enhanced by the contrast agent, the presence of microbubbles can increase the effective attenuation coefficient and diminish the strength of echo signal from the underlying tissues. The consequence of this effect is that the dilution curve measured in a region that lies below another contrast-enhanced region is attenuated. If normal techniques, based on the classic indicator dilution curves, or based on continuous infusion are used, the effect of attenuation cannot be compensated for in the measurements.

A preferred method of the present invention measures the change in intensity (in dB units), or the change in area under the dilution curves. Measuring the change (difference in dB scale, and ratio in linear scale) in signal strength, rather than the absolute values of the signal, essentially cancels out the effect of attenuation from the overlying tissue. This can be better explained quantitatively in light of Equation 1. The second term of Equation 1 takes into account the attenuation due to the contrast agent present in the overlying tissue. When this term is retained, Equations 8 and 9 take the following forms:

$$\Delta B(t) = \Delta B_{Flow}(t) + \Delta B_{VP}(t) - 4(\log e)\Delta\alpha(t)L + \quad (15)$$
$$10(\log e)\frac{k_{US} V_{ROI} t}{F}m$$

and $$\int_0^T \Delta B(t) = \int_0^T \Delta B_{Flow}(t)dt - \int_0^T \Delta B_{VP}(t)dt - \quad (16)$$
$$4(\log e)L\int_0^T \Delta\alpha(t)dt - 10(\log e)\frac{k_{US} V_{ROI} T^2}{F}m$$

If the measurements are made at two different frame rates of m1 and m2, the difference in brightness with time (i.e., the slope) is equal to:

$$\Delta B_{m2} - \Delta B_{m1} = 10(\log e)\frac{k_{US} V_{ROI} t}{F}(m_2 - m_1) \quad (17)$$

In Equation 17, the attenuation term cancels out, and the measured change in brightness is independent of, attenuation of signal from the tissue and the contrast agent. Similarly, the difference in the area under curves is independent of the attenuation effect.

$$\left[\int_0^T \Delta B(t)\right]_{m2} - \left[\int_0^T \Delta B(t)\right]_{m2} = 10(\log e)\frac{k_{US} V_{ROI} T^2}{F}(m_2 - m_1) \quad (18)$$

In summary, the preferred quantitative method and apparatus of the present invention allows measurement of flow in tissues by varying the exposure of an ultrasound contrast agent to the imaging ultrasound pulses. It is particularly important that the present invention permits multiple dilution curves to be acquired with only a single contrast injection, because prior to this invention such an acquisition had not been achieved.

Alternative Embodiments

In the alternative, the present invention provides methods and apparatus for the controlled delivery of drugs at a specific site by managing the collapse of contrast agent microbubbles. Since microbubbles decay when exposed to ultrasound, it has been proposed in the literature that these microbubbles can act as carriers of drugs to specific sites within the body. Nevertheless, the problem that remained unsolved until the present invention, was how to make the contrast-enhancing agent microbubbles collapse in a controlled fashion. A solution to this problem is, however, provided by the present invention.

As described above, the inventors have discovered that there is a relationship between blood flow, the stability of contrast agent and the exposure level to ultrasound. This relationship is defined quantitatively by Equations 8, and 9 or 18. According to this relationship, destruction of bubbles (equal to decrease in the area under the curve) is directly proportional to ultrasound exposure, e.g., frame rate. As a result, in the present invention this relationship is used to measure flow. Using the apparatus described above, the same relationship can be used conversely to cause the destruction of (that is, to break) a known percentage of microbubbles arriving in the image-field-of-view. If the desired percentage in bubble decomposition is D (%), then using Equation 8 or 9 or 18, it follows that, $$D(\%) = 100\left(\frac{m_0 - m_D}{m_0}\right) = 100\left(1 - \frac{m_D}{m_0}\right) \quad (19)$$

wherein, $m_0$ and $m_D$ are the frame rates at which bubble destruction is 0 and D, respectively. Frame rate $m_D$ can be either a very low frame rate like 0.5 fps, or it can be determined directly by making a scout-injection of contrast agent and decreasing frame rate systematically until there is no further change in video intensity (or area under the curve) with frame rate.

In summary, therefore, by varying frame rate (or any other parameter that varies exposure level) of ultrasound imaging, it is feasible to destroy a known percentage of microbubbles, and thus release the drug contained within the microbubbles at a desired location in a calculated and controlled fashion.

In addition, the invention provides methods and apparatus for improving visualization of mass and vascularity by multi-gating. Until the advent of the present invention, there has been a need for improving visualization of masses within organs like tumors. For qualitative assessment of these structures, imaging should be in real time, and the enhancement should last for prolonged periods to give an investigator sufficient time to complete his study. However, these seemingly simple requirements impose opposite demands on the scanner. On one hand, imaging at frame rates close to real time, rapidly destroys microbubbles and considerably reduces the time that the image is enhanced. On the other, the low frame-rate imaging increases the time of enhancement, but the real-time capability is lost.

In accordance with the present invention, however, methods and apparatus are provided by which image acquisition rate can be cycled at different frame rates, thereby enabling the physician to alternate between real-time and slow modes. In the real time phase (fast-frame rate) the sonographer can move the transducer to the site of imaging, and then in the slow phase observe the enhancement. By this process the sonographer can have the benefit of both real-time imaging and prolonged enhancement. Often the contrast agent saturates power Doppler images in the early stage of inflow of contrast agent. Using a gating-sequence that scans at high frame rate to selectively destroy bubbles in the early process of contrast injection, and at slow frame rate in the late stage of contrast injection, can improve and maintain the quality of visualization during the study.

The present invention is further described in the following examples. These examples are not to be construed as limiting the scope of the appended claims.

EXAMPLES

Example 1

Effectiveness of Invention by Both Gray Scale and Power Dopple Imaging

To permit multiple dilution curves to be acquired by the use of only a single contrast injection an apparatus has been developed, along with a novel, gating scheme. Briefly the apparatus comprises a laptop based computer device that allows acquisition of images at a variable rate using a commercial ultrasound scanner. Conceptually this device, which is referred to as a data acquisition controller (DACC), controls the on/off time of the scanner through the EKG port of the scanner.

The DACC generates a gating pulse sequence at a variable repetition frequency. With each gating cycle, the ultrasound image is updated with a new frame. After the initial cycle, the scanner is turned "off" until the next trigger cycle, at which point the scanner updates the image. The on/off gating cycle (GF) is varied by changing the pulse repetition rate. The DACC also controls the duration (D) for which each gating frequency is maintained. The digital waveform is buffered in the computer memory and repeated with software-timed loops until instructed by the user to stop the gating process. The decision to stop gating is made when there is no enhancement of the images required.

Figure 2:
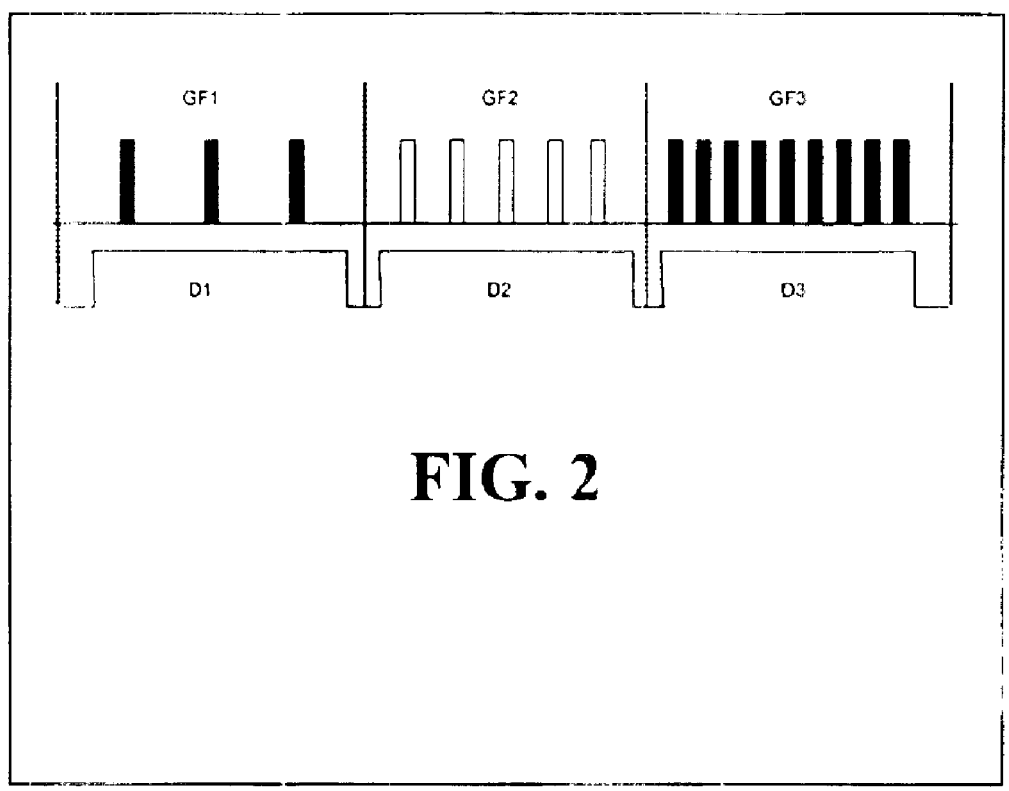
FIG. 2 depicts an example of pulse sequence. In this example, pulse sequence is made up of three different gating frequencies (GF). Each GF is maintained for a given duration. Images are acquired and digitized at each pulse. The pulse sequence D1–D3 is repeated continuously until there is no further image enhancement.

A simple example of pulse-sequence is shown in FIG. 2. Multiple pulse sequences are possible with different levels of complexities based upon the need of the imaging.

Figure 3:
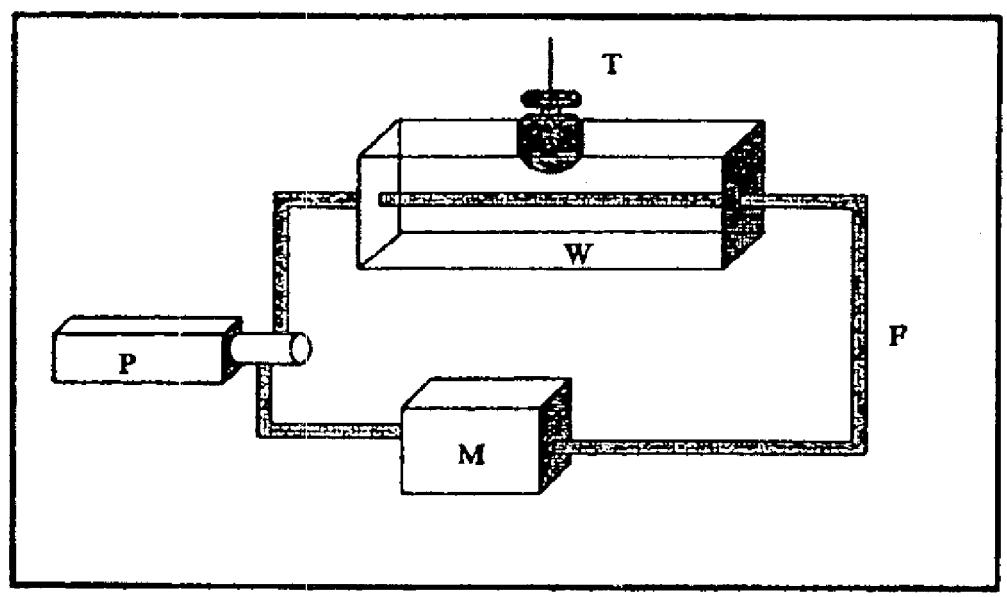
FIG. 3 depicts a block diagram of the flow phantom comprised: T=imaging transducer; W=reservoir of fluid (waterbath); P=variable rate flow-pump; M=mixing chamber; and F=flow tubing. The transducer was fixed with a clamp and aligned along the long axis of the tubing.

A study was conducted using the pulse sequence shown in FIG. 2 and the flow phantom shown in FIG. 3. The goal was to demonstrate the feasibility of the present technique. Two modes of imaging, gray-scale and power Doppler, were used for the evaluation.

Gray-scale imaging: The simplified version of the apparatus is shown in FIG. 3. The phantom comprised a flow controller, a pump, 3 mm tubing (F), a mixing chamber (M), and a reservoir of fluid (W). The tubing was imbedded in degassed saline and imaged with a broadband transducer (T). The transducer was fixed with a clamp and aligned along the long axis of the tubing. The ultrasound scanner was gated with a prototype at three different rates. This procedure alternately provided images at regular intervals at the frame rates of 0.5, 2, and 4 Hz, respectively, while keeping all of the image parameters (MI, TGC, gain etc) fixed. The total imaging time was less than 500 seconds, and the frame rates were changed approximately every 10 seconds.

Figure 4:
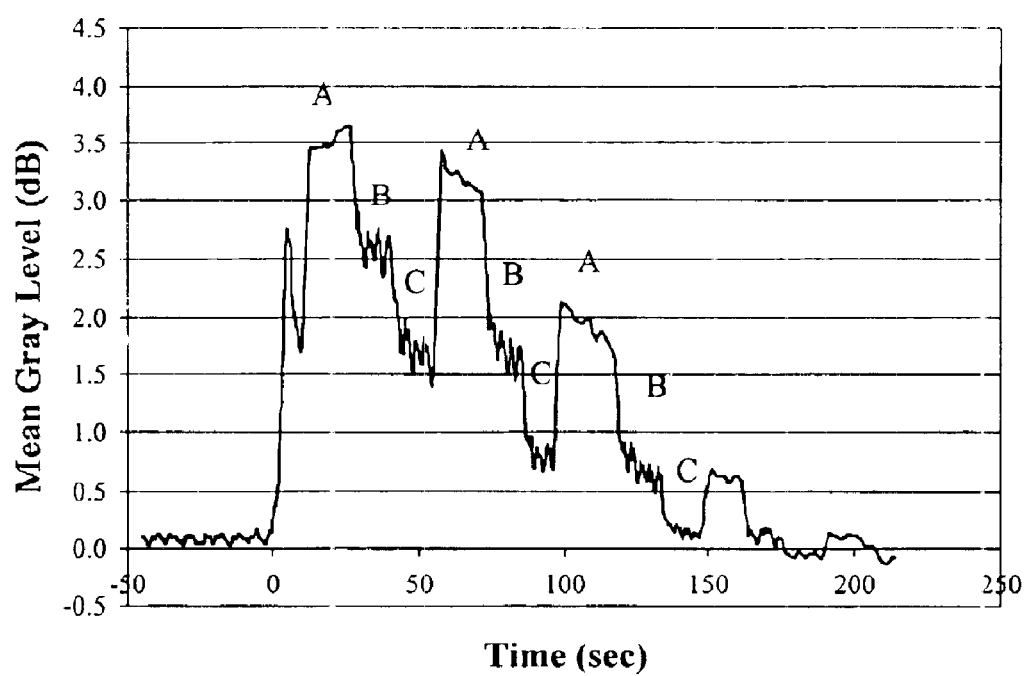
FIG. 4 graphically depicts change in image brightness during the transit of contrast agent. Images were acquired at varying rates. A=0.5 FPS; B=2 FPS and C=4 FPS. FPS= frames per second.

While keeping the flow fixed, 0.1 ml of microbubble-contrast agent (e.g., Optison by Mallinckrodt) was injected in 400 ml of solution in the mixing chamber, approximately 250 cm from the site of imaging. Following bolus injection, images were recorded using the gating method described above. The images were digitized and analyzed for mean gray level (MGL) over a fixed area of interest. FIG. 4 shows a plot of change in brightness as a function of time.

As shown in FIG. 4, each "vertical" drop in the curve represents a change in the frame rate. The "A", "B" and "C" data points on the curve were acquired at 0.5, 2 and 4 frames per second, respectively. Data corresponding to each frame rate (for example, all As) were grouped to generate three separate curves. It is important to note that by using the present invention, three different dilution curves were obtained for a single injection of contrast agent.

While the flow is fixed, there were vast differences in the three dilution curves. As the duty cycle or the frame rate is increased (i.e., from the curve formed by joining the "A" data points to the curve formed by joining the "C" data points), the area under the dilution curve becomes smaller. This behavior is consistent with the predictions based on the mathematical model. Qualitatively, the above data is in agreement with the expectations. As the frame rate increased, the bubbles were exposed to more ultrasound pulses per unit of time and this caused the bubble decay effect to dominate the imaging to a greater degree.

The above experiment was conducted at three flow pump settings. At each setting direct flow was measured by collecting liquid in a measuring cylinder. For each flow rate, change in the area under the curve and change in intensity were measured as a function of the frame rates. The area (or intensity) versus frame rate data was used to provide the best regression fit to a linear model with regression coefficient ($R^2$) exceeding 0.9. The slope and intercept for each flow rate was measured and used in Equations 13 and 14 to determine flow. The slowest flow rate was used as a reference to compute higher flow rates. The measured ratios of slope to intercept are summarized in Table 1.

TABLE 1

Flow measured by contrast enhanced gray-scale imaging obtained by varying the frame rate.

| Direct Flow Ml/min | Slope to Intercept | | Flow (ml/min) | |
| --- | --- | --- | --- | --- |
| | Area under the curve | Intensity | Using Area under the curve (Using Eqn. 13) | Using Intensity change (Using Eqn. 14) |
| 12 | −0.1663 | −0.1989 | 12 | 12 |
| 24 | −0.0865 | −0.1126 | 23.1 | 21.2 |
| 36 | −0.0602 | −0.0667 | 33.2 | 34.8 |
| | | | y = 0.94x, $R^2$ = 0.98 | y = 0.96x, $R^2$ = 0.99 |

Figure 5:
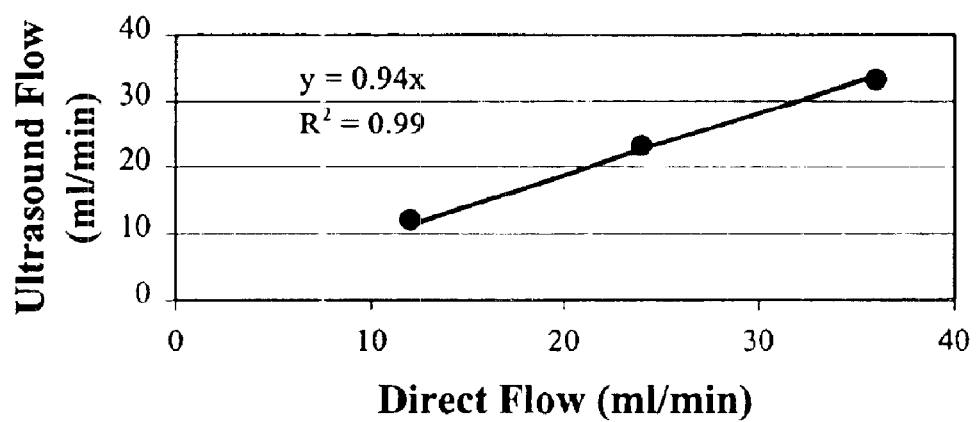
FIG. 5 graphically depicts a comparison of direct flow with flow measured by contrast enhanced gray scale imaging. Change in the area under the curve as compared with frame rate was used to measure flow.
Figure 6:
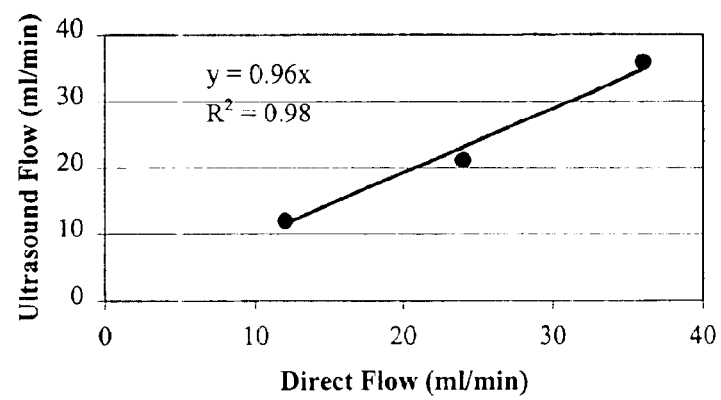
FIG. 6 graphically depicts a comparison of direct flow with flow measured by contrast enhanced gray scale imaging. Change in intensity as compared with frame rate was used to measure flow.

FIGS. 5 and 6 compare direct flow with flow measured using the contrast agent using Equations 13 and 14, respectively.

By both methods, an excellent correlation between direct flow and contrast flow was observed. The flow by contrast agent was found about 4 to 6% below the direct flow, as indicated by the slopes of 0.94 and 0.96 shown in FIGS. 5 and 6. Although the reason for this difference is not known, the difference is small and well within the confines of the experimental errors associated with measuring direct flow.

Power Doppler imaging: The mathematical formulation and experimentation described above pertain to gray-scale imaging, but as indicated earlier, the same approach can be used with other modes of imaging including harmonic and Doppler imaging. In particular, the enhancement of power Doppler images can be described by Equation 1 if ΔB in the equation represents the signal from microbubbles moving with blood above a certain threshold velocity, rather than that of all of the microbubbles. The strength of Doppler signal is coded in color in terms of the varying strengths in the images, commonly referred to as power or amplitude Doppler images. If $\overline{\Delta CL}$ is the change in color level per pixel within the region of interest due to flow of contrast agent, Equation 9 when applied to power Doppler imaging takes the form:

$$\overline{\Delta CL}(t) = (\overline{\Delta CL})_{Flow}(t) - 10(\log e)\frac{k_{US}vt}{F}m \quad (20)$$

The measurement of color enhancement with frame rate (m) during the transit of the contrast agent leads to time-intensity curves of the type shown in FIG 4. Equation 20 yields a direct relationship between flow and the ratio I/S, i.e., $$F = \varepsilon\frac{I}{S}, \quad (21)$$

wherein, ε is a constant related to instrument properties. The flow measurements made using contrast enhanced Doppler images are summarized in Table 2.

TABLE 2

Flow measured by contrast enhanced power-Doppler imaging obtained with varying the frame rate.

| Direct Flow (x) ml/min | Slope to Intercept | | Flow (ml/min) (y) | |
| --- | --- | --- | --- | --- |
| | Area under curve | Intensity | Using Area under curve (Using Eqn. 13) | Using Intensity change (Using Eqn. 14) |
| 6.25 | −0.3491 | −0.3425 | 6.25 | 6.25 |
| 13.58 | −0.1555 | −0.1761 | 14.44 | 12.15 |
| 19.64 | −0.1071 | −0.1135 | 20.95 | 18.86 |
| | | | y = 0.94 x, $R^2$ = 0.99 | y = 0.94 x, $R^2$ = 0.99 |

As was shown with regard to the gray-scale imaging, slope to intercept ratio with regard to the power Doppler imaging was determined by measuring the area under the curve or by measuring the color-level intensity. In either case, a linear correlation with near-unit slope (0.94) between true flow and the flow measured by contrast enhanced imaging was observed. As a result, the data from both the contrast enhanced gray-scale and the power Doppler imaging provides strong evidence that by using the apparatus and algorithm described above it is feasible to measure true flow using a single injection of contrast agent.

Example 2

In vivo Studies

Figure 7:
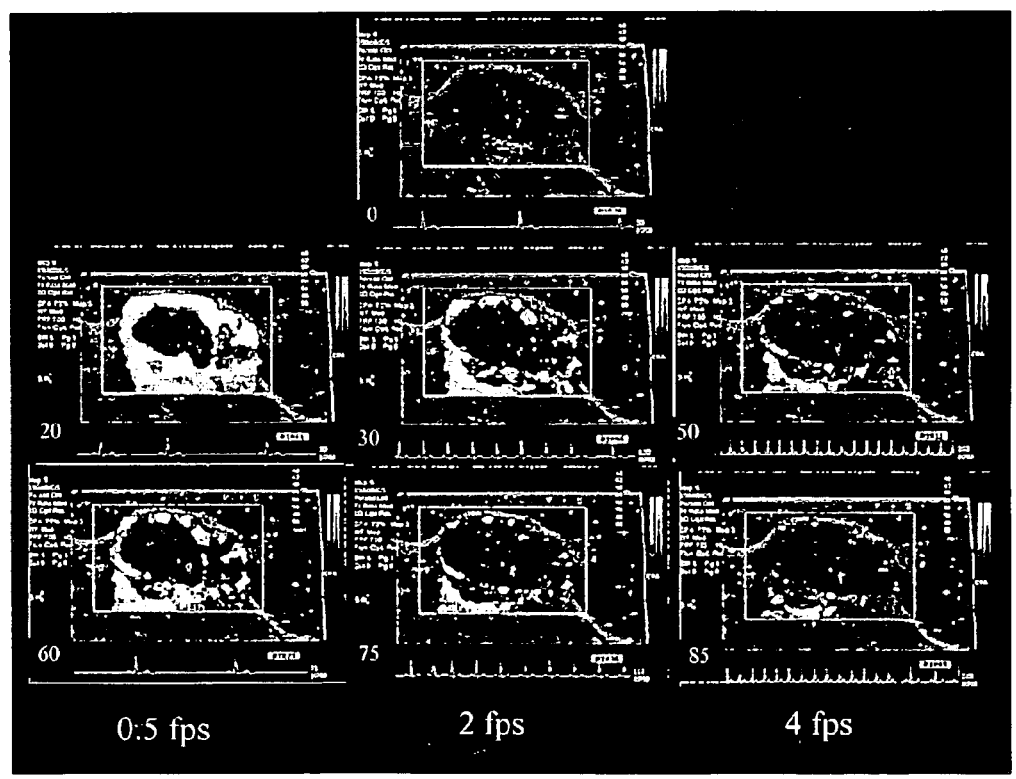
FIGS. 7A–7G photographically depict the serial enhancement of power Doppler images of a mouse tumor by a contrast agent. The numerals on each panel represent time in seconds following the bolus injection of the contrast agent.

While the phantoms provide measurements under controlled conditions, in vivo studies provide proof of the effectiveness of the invention under actual blood flow imaging conditions. To demonstrate that the method can be used to measure blood flow in real situations, measurements were made in mice by injecting 0.1 ml of contrast agent. FIG. 7 shows the change in power Doppler images as the ultrasound contrast transits through the imaged cross-section.

Power Doppler was chosen for imaging because of its higher sensitivity in detecting contrast agent (see, Sehgal et al., J. Ultrasound Med. 14:741–748 (1995)). During the transit of contrast agent, the images were acquired by varying the frame rates to 0.5, 2, and 4 frames per second (fps). The numbers at the bottom left corner of each image in FIG. 7 represent the time in seconds relative to the time of the contrast injection (e.g., 0.1 ml bolus injection of Optison). The first frame (FIG. 7A) shows an image of the tumor before the contrast agent arrived in the image plane. Clearly, no vessels can be seen. This is primarily because the conventional method does not have sufficient sensitivity to detect the flow.

As the contrast arrives in the field of view, the blood vessels in the circumference of the tumor region and the vessel feeding the tumor are enhanced. This is shown in FIG. 7B in the second row of FIG. 7.

The maximum enhancement occurs at the slowest rate of 0.5 fps. This is because at this frame rate, the exposure to ultrasound pulses is small, resulting in minimum destruction of bubbles. The enhancement is reduced as the frame rate is increased to 2 and 4 fps, respectively. This is shown in FIGS. 7C and 7D in the second row of FIG. 7. In the next cycle of change in frame rate, the images are enhanced. Compare FIG. 7D in the second row with FIG. 7E in the third row of FIG. 7.

Figure 8:
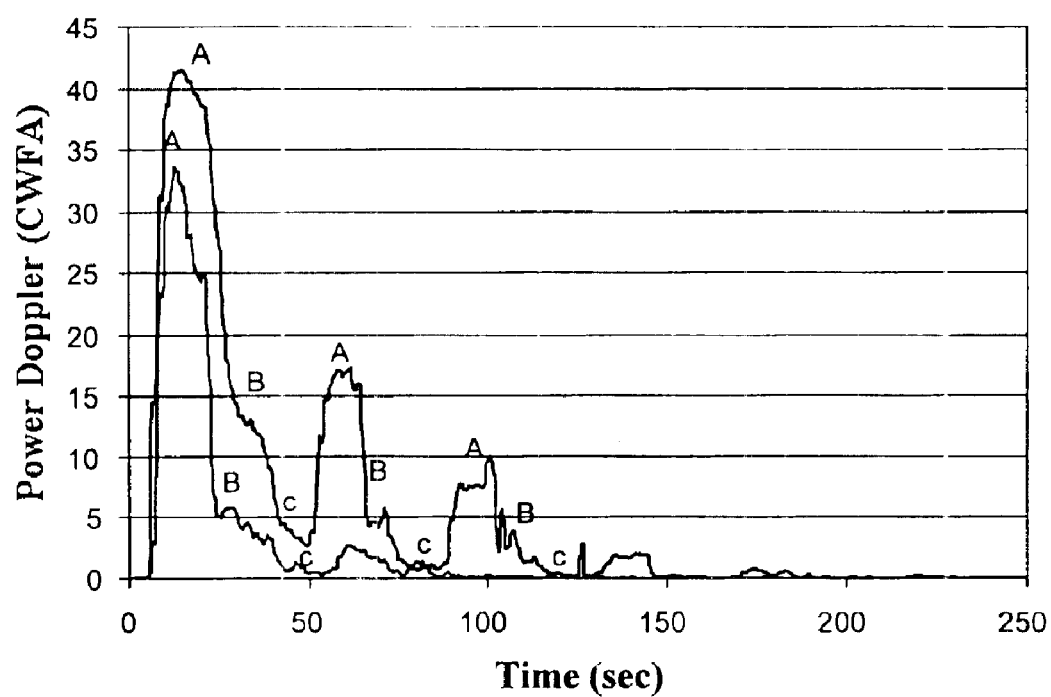
FIG. 8 graphically depicts the changes in power Doppler signal (color-weighted, fractional area) during the transit of the contrast agent. Images were acquired at varying frame rates: A=0.5 fps; B=2 fps and C=4 fps (fps=frames per second). The lines on the graph represent data from two mice. Lower (light gray) line=data from wild-type mouse. Upper (black) line=data from a mouse treated with VEGF.

Mean color level ($\overline{\Delta CL}$) within the tumor region was measured from the images. Change in $\overline{\Delta CL}$ versus time is shown for two cases in FIG. 8. The lower curve represents the flow in a wild-type (wt) mouse. The upper curve shows flow in a matched VEGF-treated mouse. It was expected that VEGF would increase the number of blood vessels, and hence, the blood flow to the tumor. In fact, the two curves in FIG. 8 show this difference.

As shown, the contrast agent lasts for a much shorter time in the wild-type mouse, as compared to the VEGF treated mouse. Moreover, the slow flow in the former case results in greater destruction of bubbles. Furthermore, the decrease in $\overline{\Delta CL}$ is much more marked in the wild-type subject, when compared to the VEGF-treated mouse. The area under the curves and the change in intensity were measured for the two curves shown in FIG. 8. Using these measurements and Equation 21, flow to the tumor was determined. These results are summarized in Table 3.

TABLE 3

Quantitative measurement of flow in mice tumors using ultrasound contrast agent.

| Tumor type | Flow measured by area under the curve (ml/min/ml of tissue) | Flow measured by Intensity change (ml/min/ml of tissue) |
| --- | --- | --- |
| Wild type | 0.44 | 0.57 |
| VEGF | 1.3 | 1.32 |

By both measurements, the VEGF-treated mouse had a higher flow rate than that which was observed in the wild type mouse, as expected. It remains to be seen, however, how the flow derived from a contrast-enhanced image compares with one using more invasive methods. Nevertheless, these results demonstrate that by varying the exposure of the contrast agent to the ultrasound pulses, it is possible to determine flow in tissues.

Example 3

Apparatus

Figure 9:
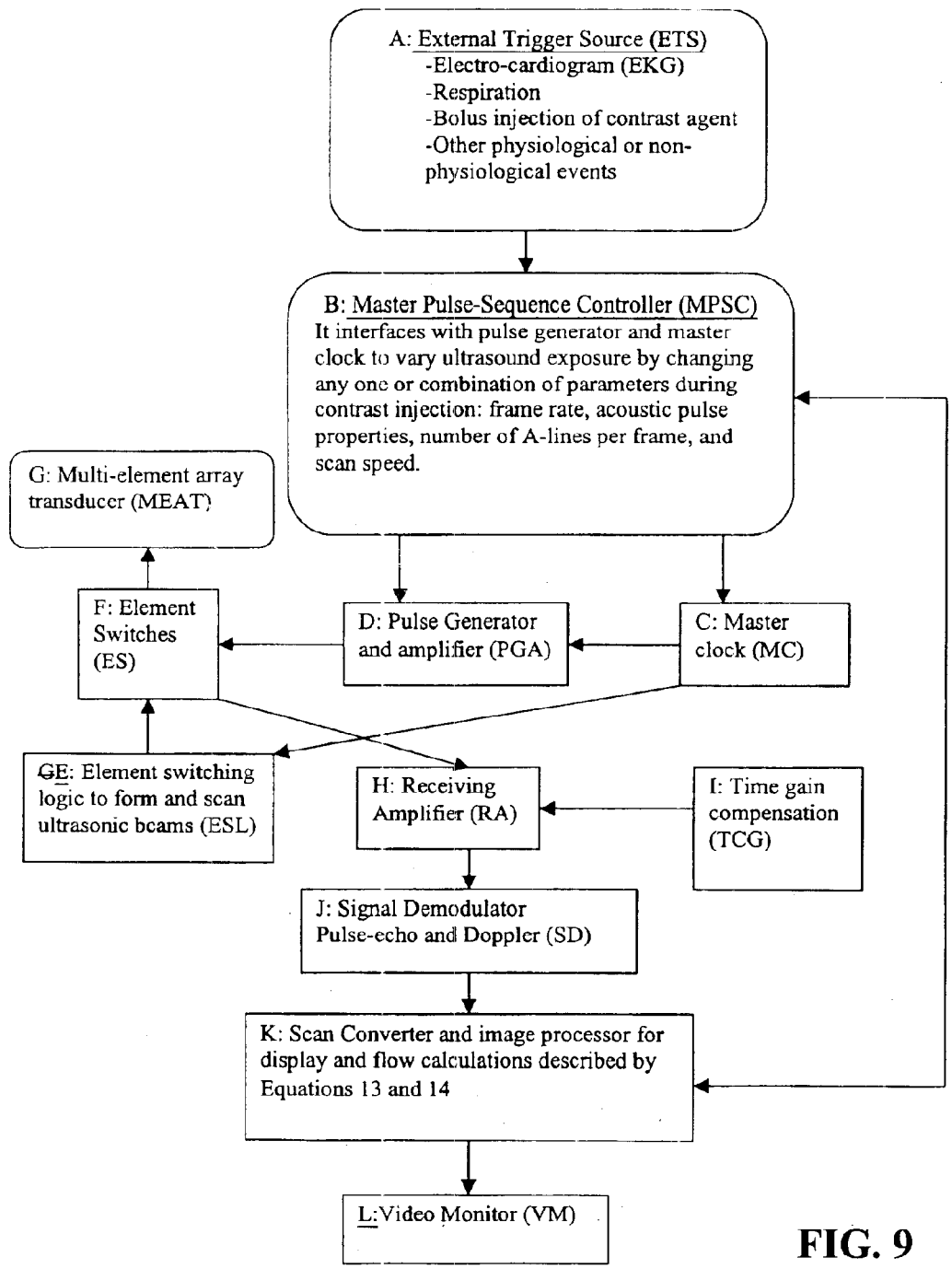
FIG. 9 shows the configuration of a conventional stand-alone scan system.

Various configurations of the apparatus are possible. In the 2D mode, the scan system could be a stand-alone system or a module that controls the operation of a conventional scanner. FIG. 9 shows a configuration of a "stand-alone" system. In the preceding examples, the apparatus was used in conjunction with a commercial scanner to generate the reported data.

Unlike conventional imaging systems, the image acquisition in the present apparatus is initiated by an external signal (ETS, Box A) either provided by a user or by provided automatically using physiological signal. Some example of external trigger are listed in Box A and include, but are not limited to ECG, respiration, bolus injection or any other physical event.

The ETS signal initiates the function of the master pulse controller (MPSC). The main purpose of this module, Box B, is to vary the exposure level during imaging. It achieves this by synthesizing a pulse sequence and using it to guide image acquisition. In the simplest form, the image acquisition is turned "on" and "off" at varying rates during contrast injection, as required by the algorithm described above. The MPSC, comprising microprocessors, interfaces with the master clock (MC) to control the pulse repetition and video rates, with the pulse generator (PGA) to control the properties of ultrasound pulses, and with the scan converter (SC) to pass the information on the pulse sequence used for acquiring images.

The components C to K are similar to those used in constructing images in a conventional ultrasound scanner (see, Hedrick et al., *In Ultrasound Physics and Instrumentation,* 3rd Edition, Mosby, Inc., St Louis, 1995 for a general description of ultrasound terminologies). The master clock synchronizes the operation of the transmit signal (Box D), transducer beam formation and echo reception, (Boxes E to G), received echo signal conditioning and analyses (Boxes H to J), and image formation and display (Boxes J to L). The image processor in the scan converter has additional functions to measure changes in image brightness and color-level of the echo (also referred to as B-scan or gray scale) and the Doppler images as a function of varying image parameters, such as, e.g., frame rate pulse length, pulse amplitude or pulse repetition frequency, and the like. The rate of change in the image properties (brightness/color level, a measure of contrast enhancement, etc.) is used to derive flow parameters.

Figure 10:
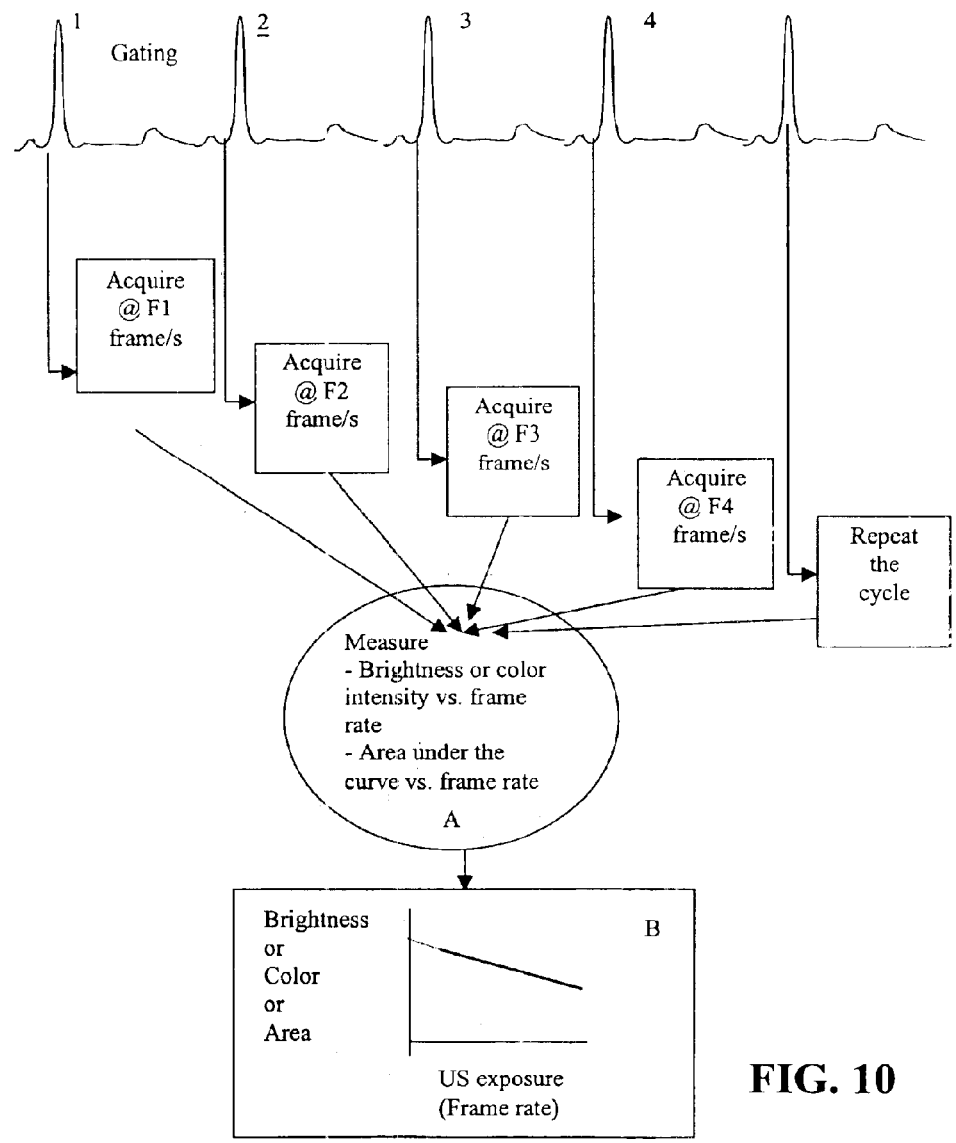
FIG. 10 is an example of the algorithm for measuring flow shown in as a graphical flow chart. The first row represents master gating pulses labeled 1, 2, 3, 4, etc. At each pulse the frame rate of image acquisition is changed. The acquired images are then analyzed for the change in echo or Doppler signal characteristics (Circle A). The rate of change in signal with frame rate is a measure of flow (Box B).

One of many possible scenarios is demonstrated by the pulse sequence shown in FIG. 10, which provides in graphical terms, an example of the algorithm for measuring flow. The first row represents master gating pulses, as shown by a sequence of pulses labeled 1, 2, 3, 4, etc. At each pulse the frame rate of image acquisition is changed. The intervals between these pulses define the time for which a given exposure level (e.g., frame rate) must be maintained. The exposure level (frame rate) is increased in a stepwise fashion at each master trigger pulse. For example, following pulse 1, the images are acquired at a frame rate of F1. Similarly, after pulse 3, the images are acquired at frame rate F3. Following the pulse 4, the cycle of pulses 1 to 4 is repeated. The rate of change in brightness (echogenicity or power Doppler signal) with exposure level (frame rate) is measured in the acquired images, and interpolated to zero frame rate in the scan converter to determine slope and intercept (Circle A). The ratio of slope to intercept is used to determine flow, using Equations 13, 14 or 21. The rate of change in signal with frame rate is a measure of flow (Box B).

Figure 11:
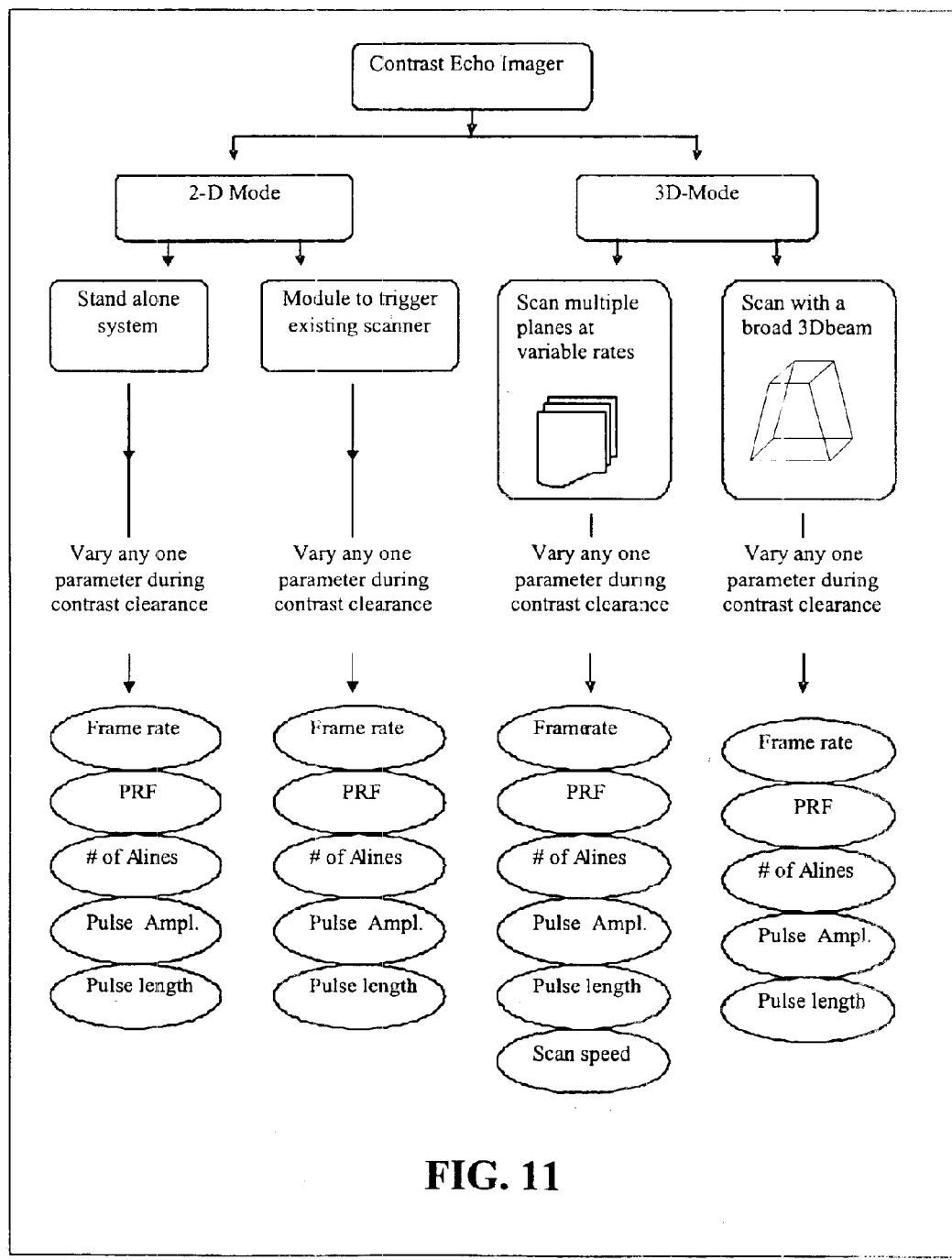
FIG. 11 depicts the configurations of 2D and 3D contrast-echo imagers. The properties circled are the parameters that can be varied individually or in combination to vary the exposure of ultrasound to contrast agent. PRF=Pulse repetition frequency.

One of the limitations of the 2D imaging mode is that it provides flow information in one plane, while the flow occurs in the three dimensions encompassing the entire organ. Although it is a common practice to make measurements in a representative plane within an organ of interest, there are definite benefits to acquiring the data in 3D. This is achieved either by scanning in 2D mode at variable speeds along the length of the organ ("scan mode"), or by increasing the beam width of the scanner so that it covers the entire organ. The overall view of various 2D and 3D modes is shown in FIG. 11.

The 3D "scan mode" is achieved either by mechanical movement of the transducer or by electronically steering the beam. Varying the speed of the scanning is equivalent to changing the exposure to ultrasound. This is illustrated with an example, wherein an organ is scanned in n steps along its length in 1 second. By comparison, if the same organ were to be scanned over 2 seconds, each plane of imaging would be exposed for twice as long, and the bubble decay would be two times as great. Consequently, changing the scanning speed can have the same effect as varying the frame rate in the 2D mode.

The alternate approach of using a broad beam that encompasses the entire organ is achieved by using a de-focusing acoustic lens in front of a transducer assembly, or by using a 2D-transducer array. Unfortunately, this leads to a significant degradation in spatial resolution of the image. The strategy, therefore, is to scan in high-resolution (narrow beam) mode to localize the middle plane through the organ, and then go to the wide-beam mode during the transit of the contrast agent.

The disclosures of each patent, patent application and publication cited or described in this document are hereby incorporated herein by reference, in their entirety.

While the foregoing specification has been described with regard to certain preferred embodiments, and many details have been set forth for the purpose of illustration, it will be apparent to those skilled in the art without departing from the spirit and scope of the invention, that the invention may be subject to various modifications and additional embodiments, and that certain of the details described herein can be varied considerably without departing from the basic principles of the invention. Such modifications and additional embodiments are also intended to fall within the scope of the appended claims.

What is claimed is:

1. A quantitative method for enhanced ultrasound imaging of fluid flow or perfusion, wherein gas-filled microbubbles are used as ultrasound contrast-enhancing agents, and wherein the method comprises:
   injecting at least one contrast agent that transits to the area or image plane to be imaged by ultra sound;
   generating and transmitting a single-beam ultrasound gated pulse sequence to the image plane, wherein the gated imaging pulse sequence varies in repetition frequency (frame rates) under the control of a data acquisition controller means,
   distinguishing removal of the contrast agent due to flow resulting from removal of the contrast agent due to bubble destruction for enhanced image processing;
   thereby synchronizing and providing acquisition of multiple dilution curves per single injection of said contrast agent(s) resulting from the varied systematic and controlled exposing of the microbubbles to the ultrasound pulses, while maintaining the signal intensity of the pulse at less than high power intensity during transit of the contrast agent(s);
   acquiring and digitizing images at each pulse; and computing changes in image brightness as a function of time during transit of the at least one contrast agent, thereby detecting changes in microbubble concentration within the image plane, independent of flow direction or attenuation of signal by selection of the at least one contrast agent or material within the plane.

2. The method of claim 1, wherein the ultrasound imaging is selected from the group consisting of gray-scale imaging, harmonic imaging, and power Doppler imaging.

3. The method of claim 1, further comprising varying systematic and controlled destruction of the microbubbles by ultrasound pulses to enable physiological measurements of vascularity and blood flow.

4. The method of claim 1, wherein each dilution curve corresponds to a different exposure level.

5. The method of claim 4, further comprising detecting change(s) in the dilution curves produced by controlling time of exposure of the microbubbles in the contrast-enhancing agent to the ultrasound.

6. The method of claim 5, further comprising visualizing and recording the change(s) between or among the plurality of dilution curves.

7. The method of claim 5, further comprising using the change(s) in the dilution curves to provide an image guided drug delivery system in a patient, wherein controlled destruction of the at least one contrast enhancing agent permits controlled drug delivery in terms of time and location of delivery in the patient, wherein prior to administration to the patient the microbubbles are charged with a drug to be delivered to the patient.

8. The method of claim 4, further comprising using a single injection of the at least one contrast agent to obtain the plurality of dilution curves.

9. The method of claim 1, further comprising using the ultrasound in vitro or in vivo.

10. The method of claim 9, wherein the ultrasound is used in vivo to visualize blood flow and vasculature within organs, tissue or tumors in a patient's body when the method is applied to the patient.

11. A device to provide quantitatively enhanced ultrasound images of fluid flow or perfusion using at least one ultrasound contrast agent comprising a plurality of gas-filled microbubbles, wherein the device comprises:
   means for providing controlled flow of a fluid;
   means for injecting at least one contrast agent into the fluid flow;
   means for generating and transmitting a single-beam ultrasound gated pulse sequence to an image plane, wherein the gated imaging pulse sequence varies in repetition frequency (frame rates) under the control of a data acquisition controller means, to synchronize and provide acquisition of multiple dilution curves per single injection of said contrast agent(s) resulting from the varied systematic and controlled exposure of the microbubbles to the ultrasound pulses, but wherein the signal intensity of the pulse remains at less than high power intensity during transit of the contrast agent(s);
   means to acquire and digitize images at each pulse; and
   means to compute changes in image brightness as a function of time during transit of the at least one contrast agent, thereby detecting changes in microbubble concentration within the image plane, independent of flow direction or attenuation of signal by selection of the at least one contrast agent or material within the plane.

12. The device of claim 11, further comprising means for distinguishing removal of the at least one contrast agent due to flow resulting from removal of the contrast agent due to bubble destruction for enhanced image processing.

13. The device method of claim 12, wherein the ultrasound imaging is selected from the group consisting of gray-scale imaging, harmonic imaging, and power Doppler imaging.

14. The device of claim 11, further comprising means for varying systematic and controlled destruction of the microbubbles by ultrasound pulses to enable physiological measurements of vascularity and blood flow.

15. The device of claim 11, wherein each dilution curve corresponds to a different exposure level.

16. The device of claim 15, further comprising means for detecting change(s) in the dilution curves produced by controlling time of exposure of the microbubbles in the contrast-enhancing agent to the ultrasound.

17. The device of claim 16, further comprising means for visualizing and recording the change(s) between or among the plurality of dilution curves.

18. The device of claim 16, further comprising means for providing a controlled imaging system.

19. The device of claim 16, further comprising means for providing an image guided drug delivery system in a patient, wherein controlled destruction of the at least one contrast enhancing agent permits controlled drug delivery in terms of time and location of delivery in the patient, wherein prior to administration to the patient the microbubbles are charged with a drug to be delivered to the patient.

20. A device to measure fluid flow or perfusion using at least one ultrasound contrast agent comprising a plurality of gas-filled microbubbles, wherein the device comprises:

computer-readable signal bearing medium;

means in the medium for computing changes in image brightness as a function of time; and means in the medium for algorithmically distinguishing the effect of removal of the at least one contrast agent due to flow from removal of the contrast agent due to bubble destruction.

21. The device of claim 20, further comprising means in the medium for automatically computing the blood flow in tissues by varying exposure of the ultrasound contrast agent (s) to imaging pulses.

22. The device of claim 21, wherein the ultrasound imaging is selected from the group consisting of gray-scale imaging, harmonic imaging, and power Doppler imaging.

23. The device of claim 20, further comprising means for varying systematic and controlled destruction of the microbubbles by ultrasound pulses to enable physiological measurements of vascularity and blood flow.

24. The device of claim 20, wherein each dilution curve corresponds to a different exposure level.

25. The device of claim 24, further comprising means for detecting change(s) in the dilution curves produced by controlling time of exposure of the microbubbles in the contrast-enhancing agent to the ultrasound.

26. The device of claim 25, further comprising means for visualizing and recording the change(s) between or among the plurality of dilution curves.

27. The device of claim 25, further comprising using the change(s) in the dilution curves to provide a controlled imaging system.

28. The device of claim 25, further comprising means for providing a controlled imaging system.

29. The device of claim 25, further comprising means for providing an image guided drug delivery system in a patient wherein the controlled destruction of the contrast enhancing agent permits controlled drug delivery in terms of time and location of delivery in the patient, wherein prior to administration to the patient the microbubbles are charged with a drug to be delivered to the patient.

* * * * *